United States Patent
Stroud et al.

(10) Patent No.: US 7,161,120 B1
(45) Date of Patent: Jan. 9, 2007

(54) GARMENT WARMING SYSTEM

(76) Inventors: Michael Maurice Stroud, 4354 Town Center Blvd. #114, El Dorado Hills, CA (US) 95762; Veronica Viloria Stroud, 4354 Town Center Blvd. #114, El Dorado Hills, CA (US) 95762

( * ) Notice: Subject to any disclaimer, the term of this patent is extended or adjusted under 35 U.S.C. 154(b) by 0 days.

(21) Appl. No.: 11/376,884

(22) Filed: Mar. 16, 2006

(51) Int. Cl.
*H05B 3/22* (2006.01)
*H05B 3/28* (2006.01)
*A45C 11/24* (2006.01)
*A45C 15/00* (2006.01)

(52) U.S. Cl. .................... 219/386; 222/146.5
(58) Field of Classification Search ............. None
See application file for complete search history.

(56) References Cited

U.S. PATENT DOCUMENTS

| | | | | | |
|---|---|---|---|---|---|
| 2,239,128 | A | * | 4/1941 | Sykes ................. | 312/400 |
| 4,163,896 | A | * | 8/1979 | McAvinn et al. ....... | 219/525 |
| 4,523,078 | A | * | 6/1985 | Lehmann .............. | 219/202 |
| 5,140,136 | A | * | 8/1992 | Fellows et al. ........ | 219/521 |
| 5,397,875 | A | * | 3/1995 | Bechtold, Jr. ......... | 219/521 |
| 5,569,401 | A | * | 10/1996 | Gilliland et al. ....... | 219/386 |
| 5,918,478 | A | * | 7/1999 | Bostic et al. .......... | 62/371 |
| 6,664,520 | B1 | * | 12/2003 | Clothier .............. | 219/634 |
| 6,693,260 | B1 | * | 2/2004 | Rodrigues ............ | 219/385 |
| 6,723,960 | B1 | * | 4/2004 | DiMartino et al. ..... | 219/386 |
| 6,774,343 | B1 | * | 8/2004 | Ibanez ................ | 219/386 |
| 6,822,198 | B1 | * | 11/2004 | Rix ................... | 219/386 |

FOREIGN PATENT DOCUMENTS

DE 3302048 A1 * 10/1983

* cited by examiner

*Primary Examiner*—Joseph Pelham
(74) *Attorney, Agent, or Firm*—Mathew J. Temmerman (57) ABSTRACT

There is disclosed a garment warming device providing a portable electrically-heated insulated water resistant and weather resistant clothing warmer having a clamshell design that warms clothing, robes, slippers, towels, blankets or other cloth-like materials placed inside it. The device further comprises a liquid tight seal preventing moisture from entering the device, as well as safety features to ensure cloth materials placed inside the device do not become dangerously hot. The device may easily stand due to a neutral center of gravity and may comprise latches and a handle capable of folding flush against the outer surface of the device.

3 Claims, 7 Drawing Sheets

GARMENT WARMING SYSTEM

BACKGROUND OF THE INVENTION

1. Field of the Invention

The invention relates to devices for warming garments and cloth-like materials.

2. General Background

It is well known that spas and hot tubs are often underutilized during the cold winter months because of the discomfort that results when one leaves a warm spa or hot tub and enters the cold air. Because the rate of heat loss is a large contributor to one's perception of temperature, and this rate is highest when one is warmest (i.e. just leaving a spa or hot tub), the cold air can feel especially chilling. Finally, humid air is a better heat conductor than dry air, so the wet surface of the skin and damp air surrounding a spa or hot tub can cause the air to seem even colder.

Conventional practice has been to quickly wrap oneself in a towel or robe, thereby minimizing as much as possible the chilling effects of the air, and removing the water from the skin. Oftentimes, the towel or robe is brought outdoors so it may be quickly obtained by one leaving the spa or hot tub. In this situation, the towel or robe is oftentimes nearly as cold as the outside air, and may be damp from being in the humid air near the pool or spa. Furthermore, a towel or robe, warm from being indoors and placed on the ground near the spa may be welcoming to spiders or insects looking for a temporary home. Such obstacles provide a strong disincentive for the spa user to even use the spa in the first place.

In the past, a number of electric heating devices have been developed, however, only a few of these are intended to be easily transportable. Additionally, some of these are not concerned with desiccation, such as those for steaming towels in a barbershop. U.S. Pat. No. 5,397,875 was intended to deal with these problems, and provided an improved portable appliance for heating towels and fluid to be used in concert with the administration of a massage. While the '875 device did provide a towel warmer with the portability and some characteristics of a brief case, it lacks any type of automatic temperature control or thermostat, and more importantly safety features to regulate the temperature. It is also somewhat limited in the items it is intended to heat.

Currently, there is no convenient, portable and safe device that will maintain at a warm temperature for a long duration, towels, garments, blankets, gloves/mittens, robes, and other cloth materials. The present invention provides a garment-warming device comprising the latest electronic safety controls that is water resistant, powered from a variety of sources and is easily transportable. Many specific advantages of the present invention are to create a more "consumer-friendly" device that simplifies the more complex garment warmers of the past.

SUMMARY OF THE INVENTION

In view of the foregoing, it is an object of the present invention to provide a device to keep robes, towels, slippers, blankets and other cloth-like materials warm and dry while one uses a hot tub during cold or wet weather.

It is a further object of the present invention to provide a convenient system allowing the user of a garment warming device to monitor and set the internal temperature of the device.

It is yet a further object of the present invention to provide a system of safety checks to ensure garments warmed in the device are not hot enough to cause burns and not hot enough to combust.

It is yet a further object of the present invention to provide a garment-warming device that may be used in myriad locations, and hence is provided with a battery and/or capability to connect to various power sources. One possible use for the device in accordance with this objective would to provide warm and dry blankets for use by search and rescue personnel who may encounter potentially hypothermic victims in cold weather emergencies.

It is yet a further object of the present invention to provide a garment-warming device capable of continuous operation over a long time period.

It is a final object of the present invention to present a simple and safe design that will maximize ease of operation for the consumer.

To achieve the above-mentioned objects, the present invention provides a portable electrically heated insulated water resistant device with a clamshell design capable of warming clothing, robes, slippers or towels placed inside it. The device further comprises a substantially liquid tight seal preventing moisture from entering the device, the capability to heat for so long as power is supplied, a thermostat, timer, and many safety features to ensure cloth materials placed inside the device do not become dangerously hot.

DETAILED DESCRIPTION

For purposes of this patent, cloth shall be defined as a fabric-like flexible material made of a network of natural or artificial fibers formed by weaving or knitting or by being pressed into felt. Materials providing the source of cloth may be natural fibers such a cotton, flax, hemp, wool, hair, silk or may be artificial fibers such as polyester and rayon.

Figure 1:
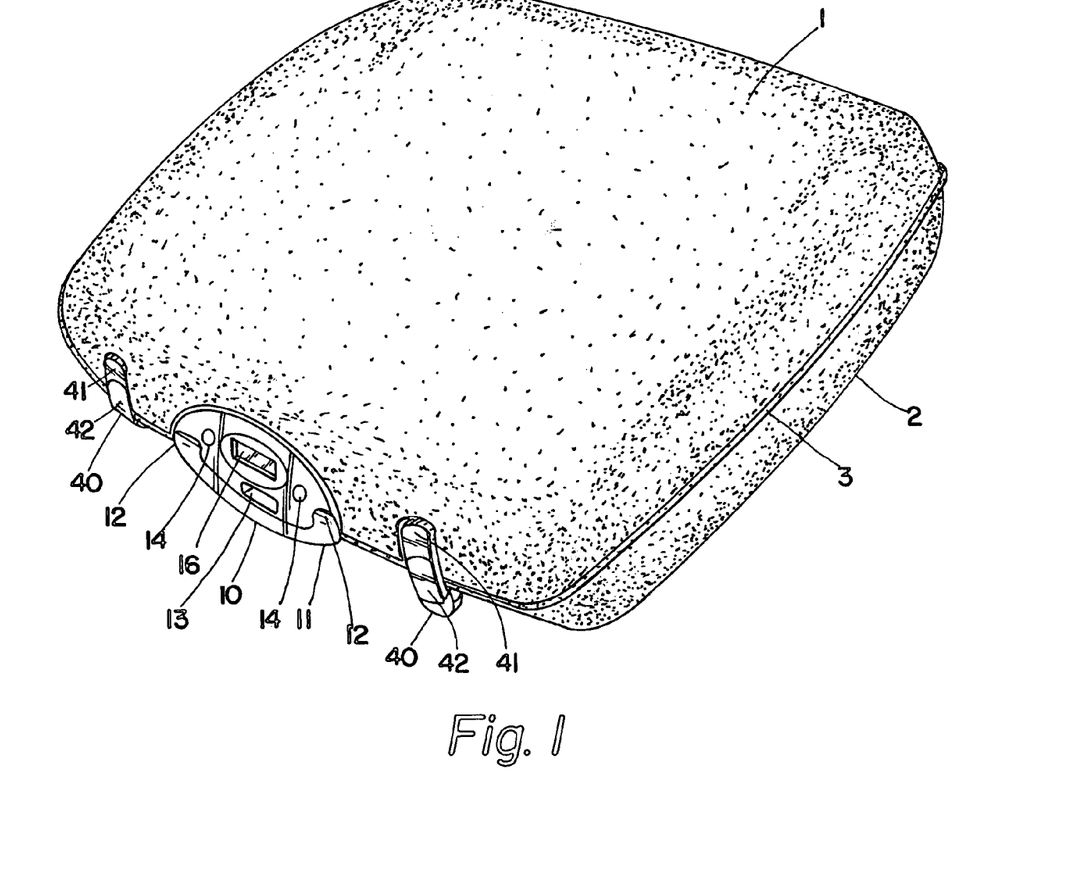
FIG. 1 is a perspective view of an embodiment of the present invention.

Referring initially to FIG. 1, the preferred exemplary embodiment of the garment warmer in accordance with the present invention resembles a spa or pool accessory with a rounded, clean and simple outer case comprising an upper lid 1 and a lower lid 2, held together by a hinge giving the device a clamshell design. In addition to this lid-supporting hinge, the garment warming device comprises a water-resistant seal 3 on the joining surface of the lids, as will be described below. The clamshell design is best exemplified in FIG. 9, wherein a phantom lid 1A is pictured in a second position, having been rotated from an initial position also shown in FIG. 9. Hinge control strap 23 prevents the relative angle between the two lids from exceeding a predetermined amount, which in a preferred embodiment is between 90 and 120 degrees.

The upper lid 1 and lower lid 2 are not limited by the material composing the lids' exterior surface, but in a preferred embodiment, a soft rubber compound is used such as a thermoplastic elastomer of the type marketed under the name SANTOPRENE® by Advanced Elastomer Systems, L. P. of Akron, Ohio (described in U.S. Pat. No. 4,130,535, which is hereby incorporated by reference) or such as a thermoplastic rubber compound of the type marketed under the name KRATON®, commercially available from Shell Chemical Co. of Houston, Tex. The texture of the exterior surface of upper lid 1 and lower lid 2 may have either a smooth surface or a grainy-like surface providing enhanced grip when the device is wet.

Figure 3:
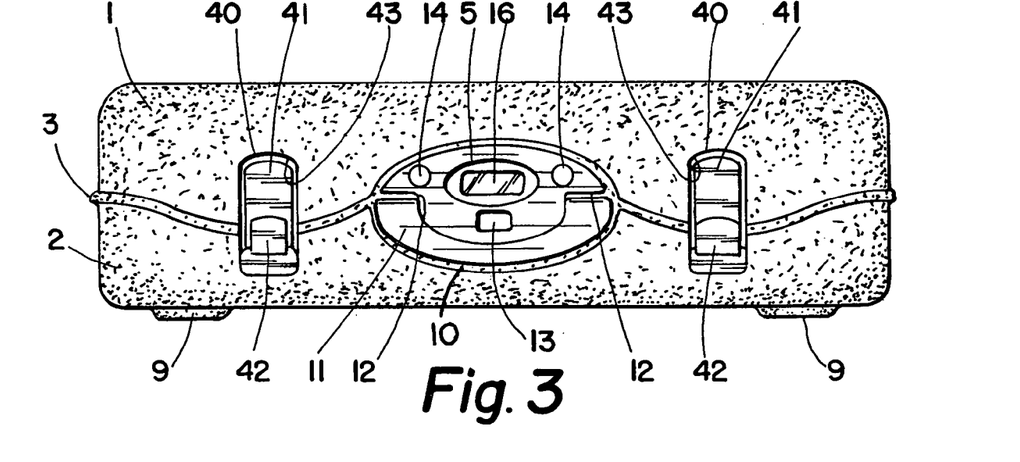
FIG. 3 is a front side view of an embodiment of the present invention.
Figure 6:
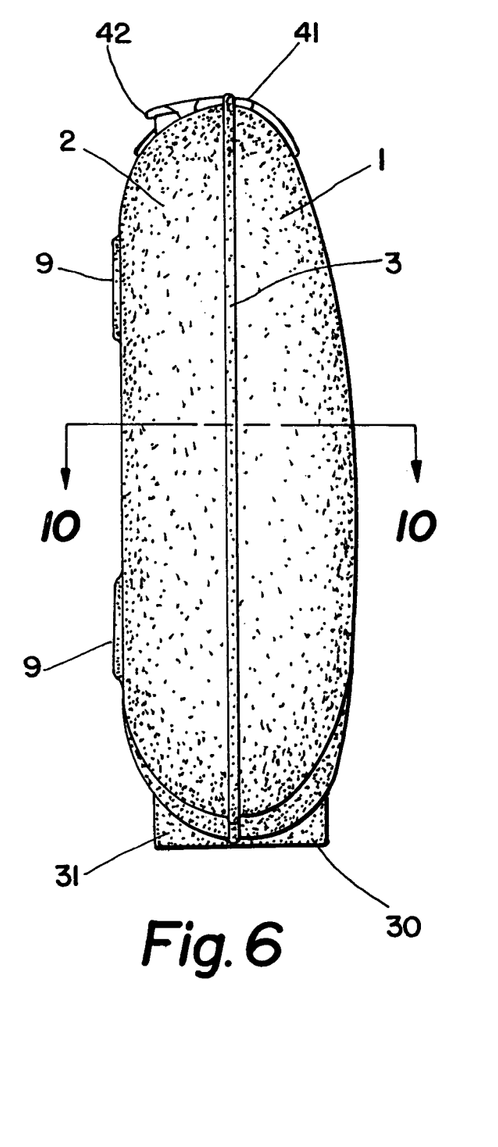
FIG. 6 is a right side view of an embodiment of the present invention.
Figure 7:
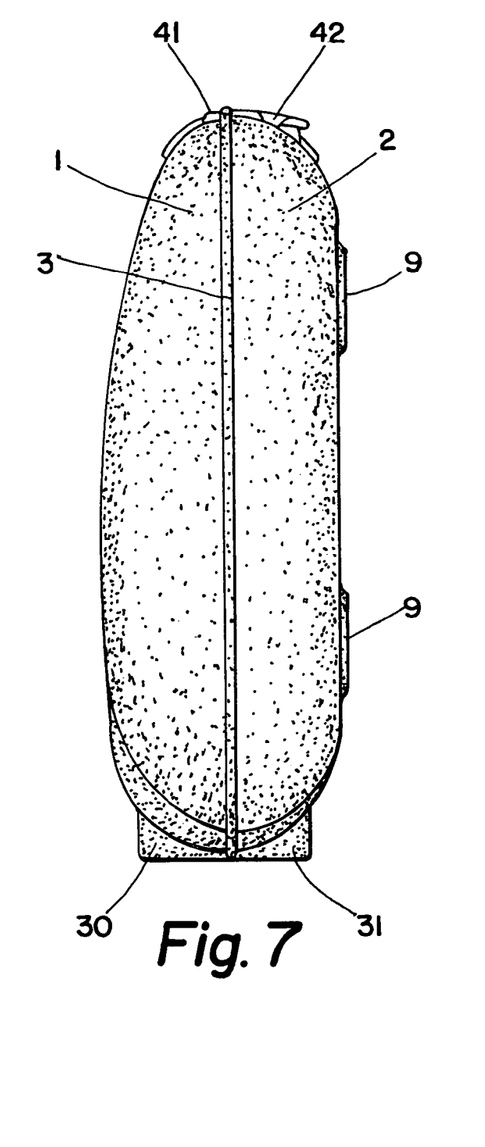
FIG. 7 is a left side view of an embodiment of the present invention.

The garment warmer may lie flat wherein lower lid 2 is substantially parallel with a ground surface (not shown). In this position, lower footpads 9 are the contact point with the ground, as shown in FIG. 3. FIGS. 6 and 7 show the depth of lower footpads 9, and in FIG. 4, a preferred embodiment is shown wherein the garment warmer comprises four lower footpads 9. Lower footpads 9 are ideally molded from the same materials as lower lid 2, but may in an alternative embodiment be affixed to said lower lid 2 and/or made of a different material. Optionally and as shown in FIG. 5, upper lid footpads 30 and lower lid footpads 31, all substantially planar, may be the primary contact point with a ground surface when the garment warmer is standing upright. Upper lid footpads 30 and lower lid footpads 31 are ideally molded from the same materials as upper lid 1 and lower lid 2, but may in alternative embodiments of the invention be affixed to their respective lids and/or made of a different material. Standing the device on the upper and lower footpads allows the device to occupy a smaller ground area, maximizing available surface space in small areas such as a storage room or cart. In this position, the provided handle 11 is also placed in a position where it may be easily grasped, aiding portability and transportability. See FIGS. 1 and 3.

In one embodiment of the invention, the size of the garment warmer is approximately 8 inches high, 18 inches wide, and 24 inches deep. This is the approximate size of a large, terry cloth robe folded in thirds lengthwise and then folded in half again. In other embodiments, any of above-referenced dimensions may be larger or smaller, as the inventive qualities of this invention are not dependent on size. One alternative embodiment contemplated by the applicants involves reducing all the dimensions of the embodiment described above such that a "baby" version of the garment warmer may be used to warm clothes suitable for infants and children between the ages of one and three. In this configuration, the device is ideal for warming small blankets when traveling, or for warming a child's towel or clothing for use after a bath or after the child has spent time in cold outdoor weather.

Figure 2:
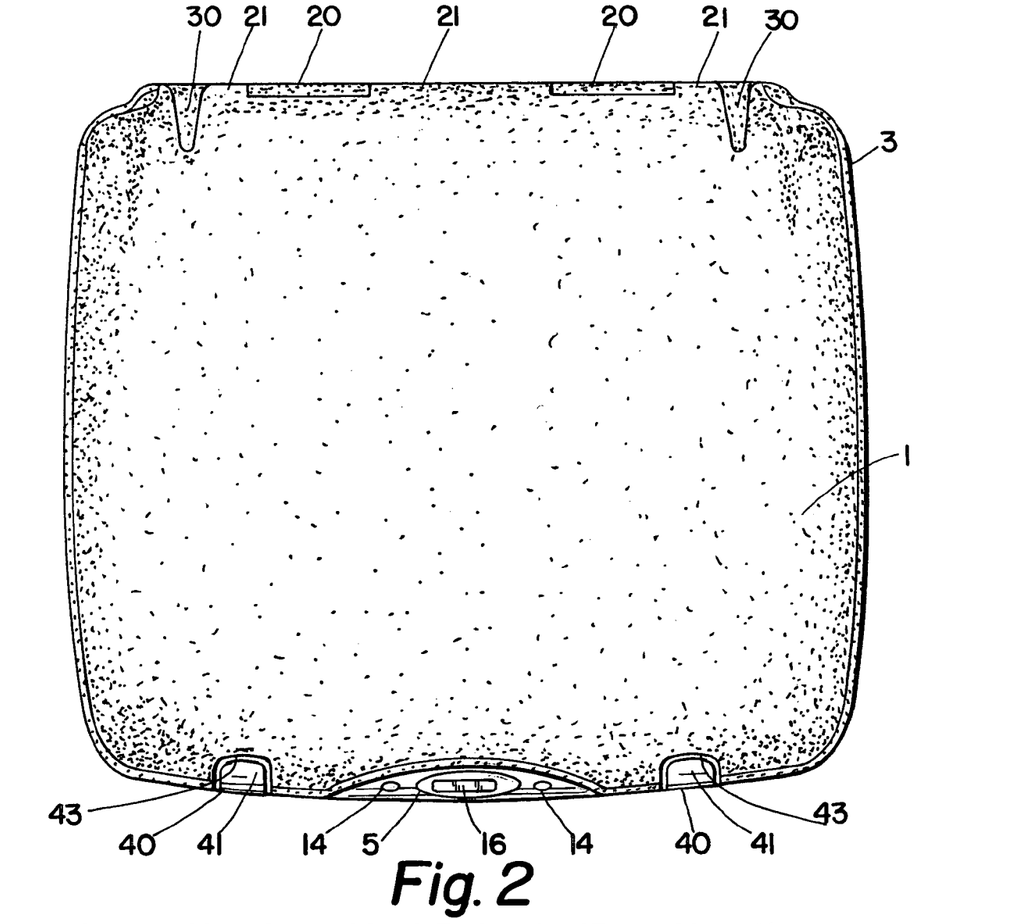
FIG. 2 is a top plan view of an embodiment of the present invention.
Figure 4:
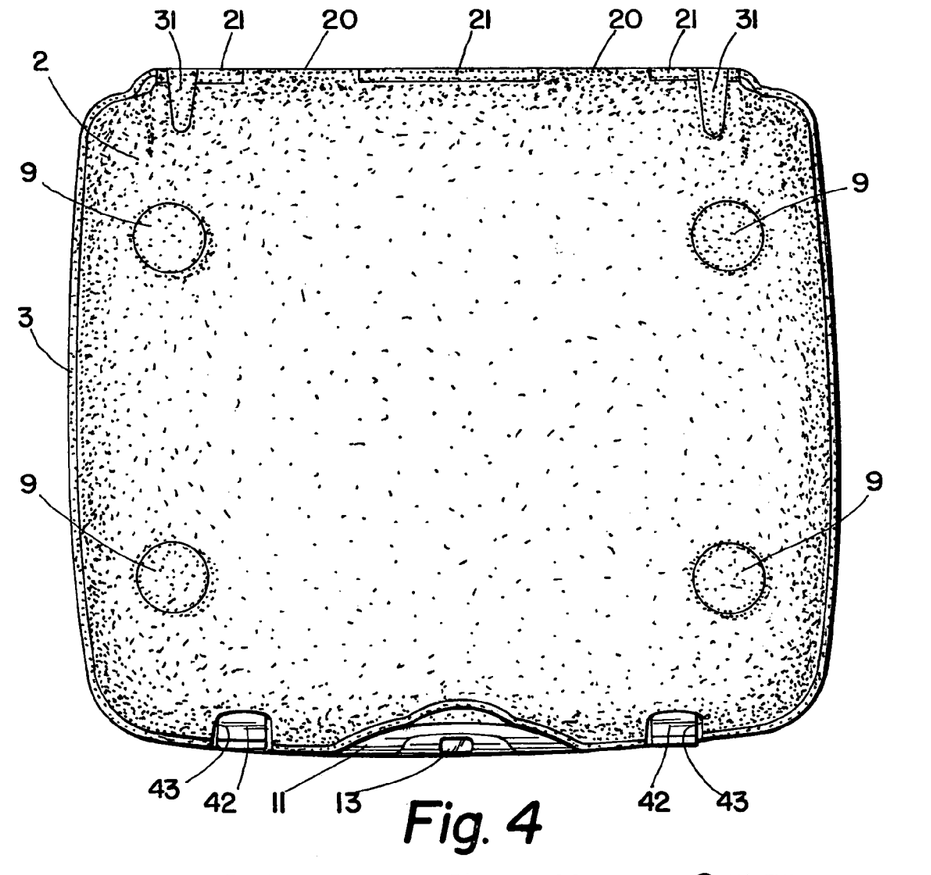
FIG. 4 is bottom plan view of an embodiment of the present invention.
Figure 5:
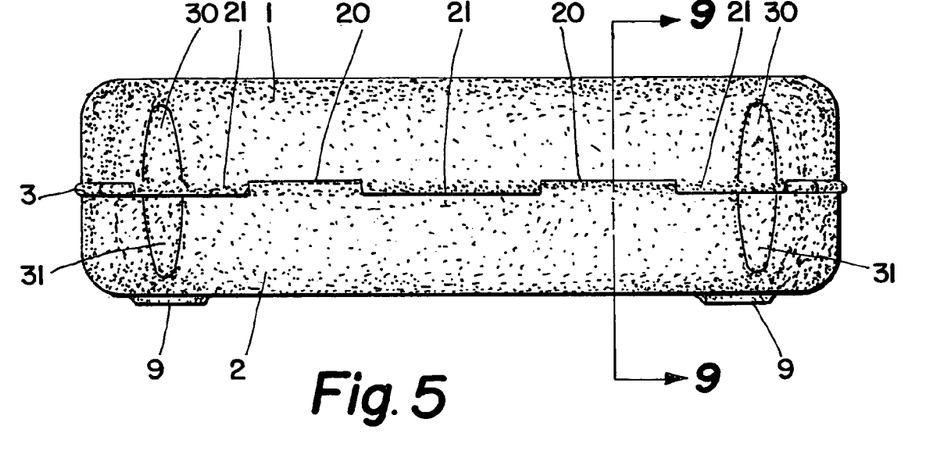
FIG. 5 is a back side view of an embodiment of the present invention.

In a preferred embodiment, a hinge is composed of a lower lid hinge 20 and an upper lid hinge 21, as shown in FIGS. 2, 4, and most clearly in FIG. 5. Continuing to focus on FIG. 5, attention is drawn to the preferred embodiment where said lower lid hinge 20 is an extension of said lower lid 2 and said upper lid hinge 21 is an extension of said upper lid 1. Lower lid hinge 20 and upper lid hinge 21 are aligned such that a provided hinge pin 6 extends substantially the length of both hinges. See FIG. 9. The garment warmer in a preferred embodiment comprises the hinge as described here and as is well known in the art, but other hinge systems also well known in the art may be optionally used instead.

Because the warmed garment is likely to be used near water or in wet weather, the garment warmer must be water resistant to protect the electrical components therein. Seal 3, positioned between the outside elements and the internal elements of the device helps insulate the inside of the device from the external environment. While the seal 3 is primarily for retaining heat within the device, it also serves as a barrier to external liquids, aiding in the overall water-resistance of the device. As the upper lid 1 and lower lid 2 are moved to a closed position about said hinge, said seal 3 is compressed by the joining surfaces of said lids. The seal 3 is configured such that the pressing force of the two lids is sufficient to hinder the flow of liquid or moisture therebetween. As shown in FIGS. 1 and 2, said seal 3 is formed around substantially the entire radially outer perimeter of the joining lids. The seal 3 also extends around latches 40 as shown in FIG. 3, and surrounds a display/handle unit 10, as shown in FIG. 1. In the preferred embodiment of the invention, seal 3 is affixed to the upper lid 1, but alternatively the seal may be affixed to the lower lid 2 or to both upper lid 1 and lower lid 2.

The garment warmer comprises at least one latching member, and more particularly as shown by the exemplary embodiment in FIG. 1, latch 40. Although in this embodiment latch 40 secures the upper lid 1 and lower lid 2 in the closed position, other latching members may be employed. As shown in FIG. 1 and FIG. 3, the latches 40 are ordinary latches as are common in the art, in a preferred embodiment comprising a first latch part 41, and a second latch part 42. The latch 40 operates partially within a latch indentation 43, as shown in FIGS. 2 and 3. Latch indentation 43 is ideally sized such that when the latch 40 secures upper lid 1 and lower lid 2, said latch is substantially flush with said upper lid 1 and lower lid 2. As the garment warmer is intended to be operated in an environment where there is a chance it may be exposed to liquid, said latches 40 are ideally constructed of a material substantially resistant to the oxidative effects of oxygen and water.

FIG. 3 provides the clearest view of the display/handle unit 10 comprising among other components, a handle 11 and a display 16. The display/handle unit 10 is molded as one unit and is inserted and sealed into lower lid 2. When the case is closed as shown in FIG. 3, the display/handle unit 10 is secured approximately in the center of the horizontal outer surface of the device and is surrounded by an extension of seal 3. Because the display/handle unit 10 comprises several components including the electronics that control the heated pads and a display 16, other waterproofing means are employed, such as a display/handle unit seal 5, which makes display 16 resistant to damage by water.

Handle 11 is preferably of a design well known in the art, and is preferably constructed of a material substantially unaffected by moisture, such as natural or synthetic rubber, or hard plastic. A handle hinge 12 allows said handle 11 to rotate from a position substantially flush with upper lid 1 and lower lid 2 to a position substantially perpendicular to said lids, facilitating the portability of the garment warmer.

As indicated above, the handle 11 is in a preferred embodiment a part of a structure also comprising display 16. Various display technologies may be used in conjunction with the display 16, such as light-emitting diode, vacuum fluorescent display, liquid crystal display technologies or others. The display is a segment display system although in alternative embodiments more advanced screens may be employed.

The display/handle unit 10 further comprises electronic controls 14. In the preferred embodiment and as shown in FIG. 3, the electronic controls 14 comprise buttons that control the internal temperature of the garment warmer. The electronic controls may themselves include a light source facilitating the user's operation of the device during the nighttime. In a separate embodiment, the electronic controls may be simpler, controlling only the on and off status of the device. In still separate embodiments, other features such as thermostat, thermostat timer, and clock may be controlled by the electronic controls 14. The timer function allows the user to set the device to begin power on at a predetermined time. While in the preferred embodiment the electronic controls 14 comprise two buttons, in other embodiments the number of buttons may be less than or more than two. Ideally, the buttons will be covered by a waterproof membrane as is well known in the art. The display can show the time of day, the internal temperature of the device, or can alternate between time and temperature, displaying each for approximately 4 seconds.

The display/handle unit 10 in the preferred embodiment of the invention also comprises a plug receptacle 13, to which a coupler 83 is inserted thereto. See FIGS. 1 and 8. Attention is drawn to coupler 83 on FIG. 8, which is a part of a power supply unit 80, comprising power converter 81, DC power cable 82, and coupler 83. Typically, the device will be connected to a domestic AC power plug and socket through a power plug (not shown), but may be used with a variety of plug types, power supply frequencies and voltages. The device is an AC-DC device, and as such may easily be connected to a boat or car's DC system, provided the optional power supply cords (not shown) are used. The plug receptacle 13 has a seal ring to allow use in wet weather, and a grommet cover to cover the plug when not in use.

In a preferred embodiment power is supplied to the garment warmer through a direct connection (power cable) to an external power source. The device may in an alternative embodiment comprise batteries (not shown) that provide lasting power when a direct connection is not available. Ideally, the device will utilize rechargeable batteries that may be re-charged after they have been drained. Various types of batteries may be used such a standard lead acid rechargeable battery, or more complex batteries such as nickel-cadmium, nickel metal hydride, lithium-ion cells, and others. The batteries used by the device may be of nearly any size capable of fitting within the upper and lower lids, and may be custom sized so as to occupy a minimal amount of usable interior volume. Finally, to maintain the balance of the system while it stands upright, the batteries may be placed so as not to disrupt the neutral center of gravity.

Figure 8:
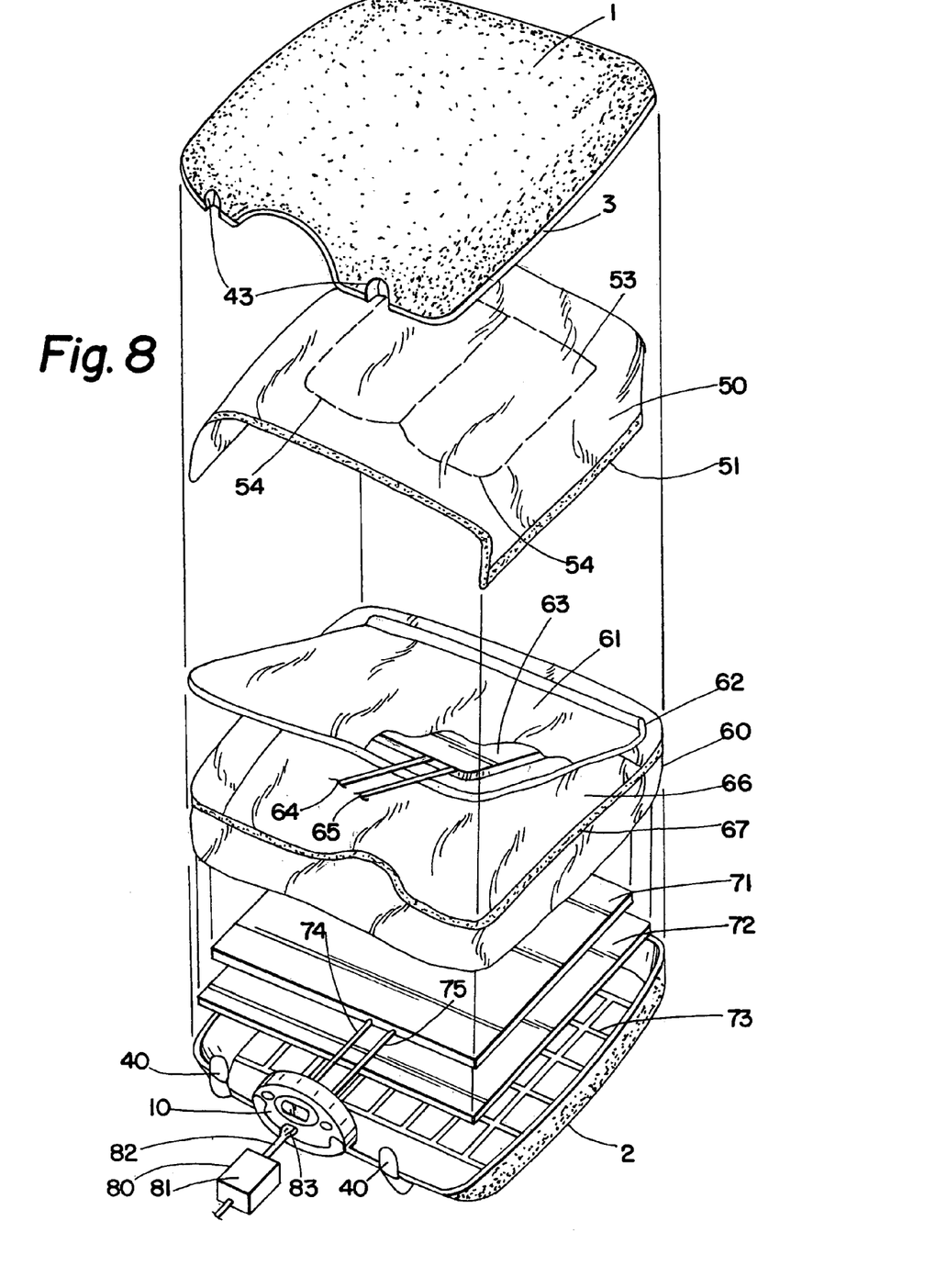
FIG. 8 is an exploded perspective view of an embodiment of the present invention.
Figure 9:
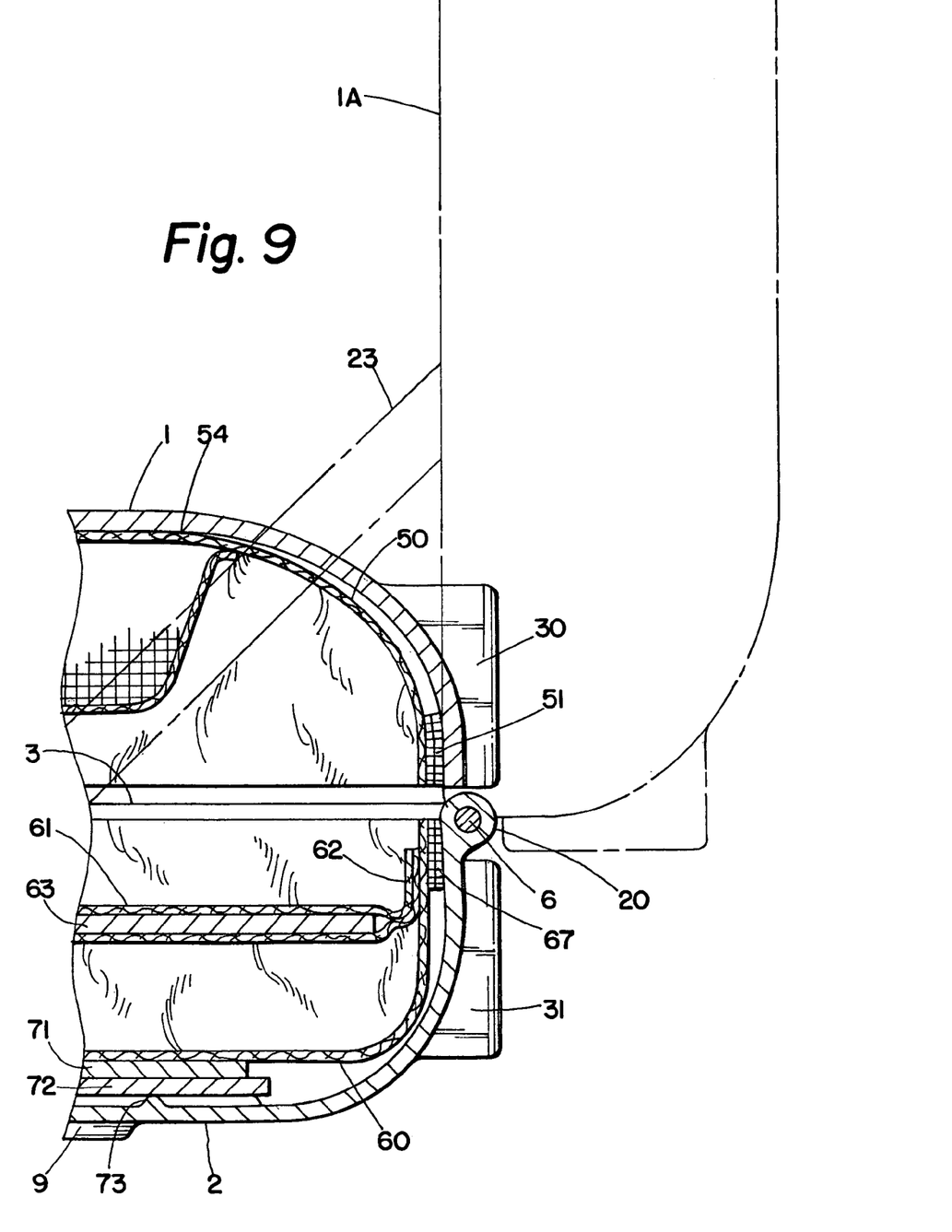
FIG. 9 is a cross sectional view of an embodiment of the present invention taken at FIG. 5 line 9—9.
Figure 10:
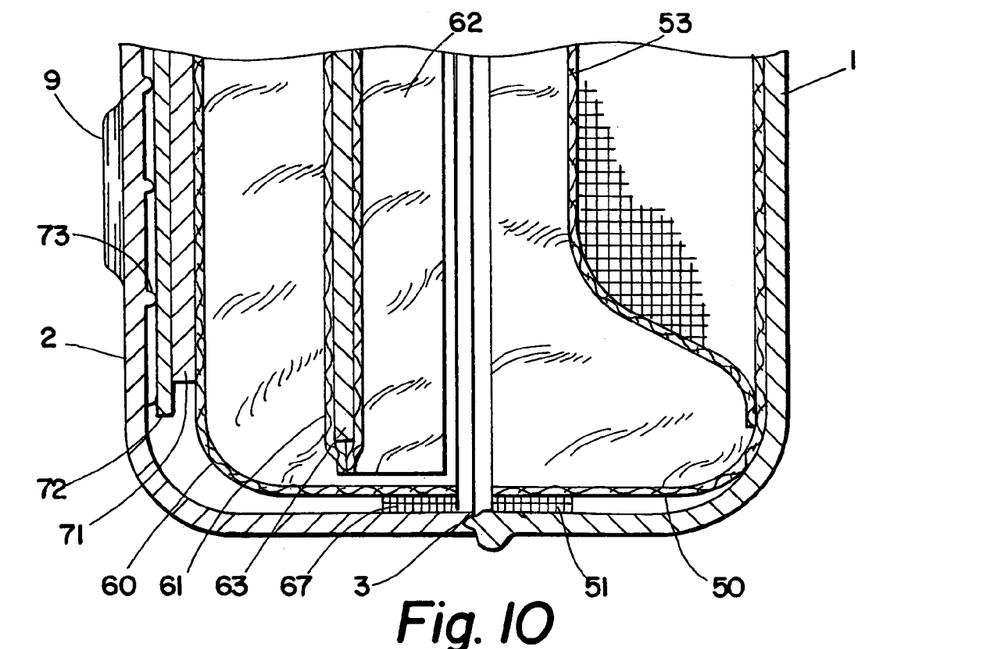
FIG. 10 is a cross sectional view of an embodiment of the present invention taken at FIG. 6 line 10—10.

Attention is now directed to FIGS. 8, 9 and 10, which show the internal compartments of the garment warmer. The design is intended to allow the effective distribution of heat through the robe, cloth or garment. Numerous sectional members define several compartments inside the device, including one compartment for storing and warming slippers.

An upper lid layer 50 and a lower lid layer 60 define the primary internal compartment, as shown in FIG. 8. This primary area is then separated by a heated middle pad 61, which is the preferred heating element in the device. Heated middle pad 61 is moveable about heated middle pad hinge 62, and is moveable along an arc similar to upper lid 1 as upper lid 1 rotates about upper hinge 21. In this way, the user of the device may swing open upper lid 1 along upper hinge 21, and then proceed to similarly swing open heated middle pad 61, exposing a lower lining 66. See FIGS. 8 and 9.

Continuing to draw attention to FIGS. 8 and 9, heated middle pad 61 substantially encases a middle heating element 63. Middle heating element 63 is connected to the power supply unit via middle heating element first wire 64 and middle heating element second wire 65. Electrical current flowing through middle heating element 63 encounters resistance, resulting in the heating of the element. The heating element may use nichrome wire as the conductor, or any other conducting material commonly known in the art.

Upper lid layer 50 is affixed to the inner side of upper lid 1 and ideally comprises insulative cloth. See FIGS. 8 and 9. Upper lid layer 50 is also a likely point of contact with articles placed inside the device for heating and as such is provided with a low thermal conductivity to prevent heat loss to the environment external to the garment warmer. A cloth or fabric made of natural or artificial fibers and having a thermal conductivity of less than $0.2$ $W \cdot m^{-1} \cdot K^{-1}$ at a temperature of between 0 degrees and 100 degrees Fahrenheit is the preferred material of upper lid layer 50 covering the side facing heated middle pad 61. The material of upper lid 50 will also safely conduct heat up to 180 degrees Fahrenheit, which is beyond the 170 degree maximum operating temperature of the device. Other cloth-like materials that reduce the flow of heat through them may similarly be employed, including but not limited to fiberglass, polystyrene foam, polyurethane foam and a rubber composite-like material. This attention to insulation helps maintain heat within the device, thereby decreasing heat times, and increasing efficiency and battery life.

Upper lid 50 also comprises a slipper bag 53. See FIGS. 8 and 9. This bag is ideally affixed on three sides to upper lid insulating layer 52, thereby creating on the fourth side a slipper bag opening 54 through which a user may insert slippers or other small articles into slipper bag 53 for warming or heat retention. See also FIG. 10a.

Immediately attached to upper lid layer 50 are hook-and-loop fasteners, such as Velcro® in a structure hereinafter termed upper lid layer Velcro® 51. It is known that other Veclro®-like materials or fasteners may easily be substituted. Lower lid layer 60, of similar construction to upper lid layer 50, also comprises a similar lining of insulation hereinafter termed lower lid layer Velcro® 67. As the device opens and closes in a clamshell fashion as previously described, these two Velcro® layers will come into contact and create a secure inner heated compartment for the storage of garments or cloths.

In an alternative embodiment, the upper lid may also comprise a second heated upper pad insert (not shown). The second heated upper pad insert may be attached to the upper lid layer 50 or to another contact point on the inside of upper lid 1. The second heated upper pad insert may be a flap that may unfold to an open position similar to the operation of an accordion or accordion-style briefcase. This allows the flap to occupy a minimum of space when not in use, but when opened provides a space to contain slippers or other small articles placed inside it. Power provided to the heated upper insert will be provided in a similar fashion to that described in the middle heating element 63 portion of this application.

Lower lid layer 60 is affixed to an inner side of lower lid 2 and is ideally composed of insulative cloth. Like upper lid layer 50, lower lid layer 60 will come into contact with garments or cloth placed inside the device and thus comprises a material having a low thermal conductivity. A cloth or fabric made of natural or artificial fibers and having a thermal conductivity of less than 0.2 W·m$^{-1}$·K$^{-1}$ at a temperature of between 0 degrees and 100 degrees Fahrenheit is the preferred material covering the side of lower lid layer 60 that faces heated middle pad 61. As described regarding upper lid layer 50, other, similar low conductivity materials may be used.

Between lower lid layer 60 and lower lid 2 is heated lower insert 71. See FIGS. 8 and 9. Similar to heated middle pad 61, heated lower insert 71 receives its power from heated lower insert first wire 74 and heated lower insert second wire 75, as shown in FIG. 8. Heated lower insert 71 substantially encases a lower heating element (not shown) which functions similarly to heating element 63, and may likewise be composed of nichrome wire or another conducting material commonly known in the art.

Between heated lower insert 71 and lower lid 2, and affixed to an inner side of lower lid 2 is lower lid insulating layer 72, ideally composed of insulative cloth. As lower lid insulating layer is not a likely point of contact with garments or cloths placed inside the device, it can be designed from a purely functional standpoint. As such, its primary purpose is to prevent heat loss to the environment external to the garment warmer, and as such is made of material having a thermal conductivity of less than 0.2 W·m$^{-1}$·K$^{-1}$ at a temperature of between 0 degrees and 100 degrees Fahrenheit. More preferably, its thermal conductivity is less than 0.1 W·m$^{-1}$·K$^{-1}$ at a temperature of between 0 degrees and 100 degrees Fahrenheit. The material of lower lid insulating layer 72 will also safely conduct heat up to 180 degrees Fahrenheit, which is beyond the 170 degree maximum temperature of the device. Materials including but not limited to fiberglass, polystyrene foam, polyurethane foam, a rubber composite like material, and other low conductivity materials may be used as described regarding upper lid layer 50.

The final structure positioned in the lower lid is a lower lid raised grid 73, which is clearly shown in FIG. 8. For everywhere but the points of contact between the insulating materials and the raised grid, the raised grid creates a layer of air between the lower lid 2 and said insulating materials. In this way, the only points of contact between the insulating materials inside the device and the lower lid 2 (which is exposed on one side to outside air) are at the raised grid, thereby reducing the amount of heat lost through conduction.

Figure 10A:
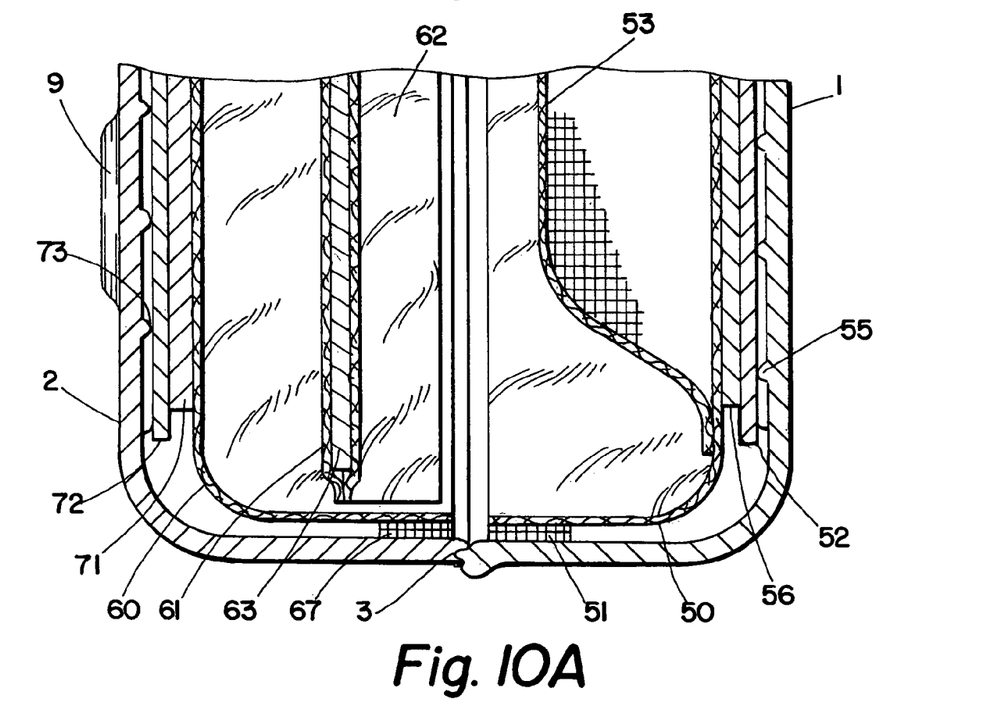
FIG. 10A is a cross sectional view of an alternative embodiment of the present invention taken at FIG. 6 line 10—10.

In an alternative embodiment of the invention, the upper lid 1 further comprises an upper lid raised grid 55, a cross section of which is shown in FIG. 10A. The overall structure and function is analogous to lower lid raised grid 73 as shown in FIG. 8. The upper lid raised grid 55, like the lower lid raised grid 73, utilizes a layer of air, having an extremely low thermal conductivity, to minimize heat loss. In the embodiment comprising the upper raised grid 55, the garment warmer further comprises an upper lid insulating layer 52. This layer is of a construction similar to lower lid insulating layer 72, and likewise has a primary purpose of preventing heat loss to the external environment. In this alternative embodiment of the invention, the upper lid 1 further comprises a heated lid insert 56.

The level of sophistication of the electronic components inside the device differs among the various embodiments of the invention. In the embodiments containing a thermostat and timer, more complex electrical circuitry and components will be needed. Regardless of the level of sophistication and complexity, an objective of the invention is to protect these electronic components from the nearby heat radiating outward from heating element 63. Thus, the electrical wires in the device are robust enough to withstand repeated heating and cooling. The display 16 and its related components must also be protected from the heat generated by the device. Therefore, insulating materials (not shown) between those components and the device heating elements are provided.

An additional object of the invention is to warm garments and other cloth-like materials safely. Thus, to prevent an unintended exothermic reaction in the clothing placed very near a heating element, safety measures have been incorporated. For instance, ensuring no direct contact between the heat element and the clothing will decrease the chance of clothing ignition. Furthermore, the device comprises a safety automatic shut-off feature which disables the device should a predetermined maximum internal temperature threshold be reached. In a preferred embodiment this is simply a relay breaker controllable by a sensor that monitors the temperature of the warming pads. The display 16 may indicate whether a shut-off or other malfunction has occurred. The maximum temperature allowance of the device (170 degrees) is lower than the kindling point of a typical cloth, thereby ensuring there is nearly a zero chance for combustion. Optionally, safety shut-offs activated in the presence of smoke or smoldering clothes may also be employed as a secondary safety mechanism. These plus other safety features will ensure the device meets various electronic certification regulations in various countries around the world.

As has been described above, it is an object of the invention to provide protection from water for the various electronic components composing the device. Thus, a playful splash or adverse weather such as rain or snow will not substantially penetrate seal 3, latch 40, or display/handle unit seal 5. Optionally, the level of water resistance may vary with the intended use of the device. Intended uses near water may include boating, camping, near a pool or hot tub, and skiing.

The garment warmer may be used by anyone who would like a warm towel or robe with which to wrap themselves. This is especially enticing when one is expected to be outdoors in a spa or hot tub during the cold fall and winter months. Although in an alternative embodiment, a battery pack provides a source of constant heat and hence even more portability, the case design coupled with its various layers of insulation provide lasting heat retention even without a battery as a lasting heat source.

The garment warmer can be heated in one of two fashions. It is expected that most users will plug the device into a typical residential electrical outlet, and heat the device prior to taking the device outside. Once outside, the user may enjoy himself or herself knowing that the device's insulation and optional internal battery powered heating element(s) will ensure their clothes are warmed, and said seal 3 will keep their clothes dry. Even without a battery pack or if the battery is not charged, the insulation alone will keep the clothes warm and dry for significantly longer than they would be just being left exposed to the elements.

In another expected use of the garment warmer, the user will not preheat the device as described above, but will instead simply place his or her clothing and towel in the device and immediately go outside. In this scenario, the battery alone will power the heating element, either immediately or after a preset amount of time, which in turn will raise the temperature of the materials placed inside, again ensuring warm and dry clothing and towels await the user once the user is done enjoying him or herself in the spa or hot tub. With both functions, the display 16 has the capabilities to keep the user informed as to temperature, time and timer status. In the latter function, the battery life is extended by delaying the heating process, thereby avoiding heating the cloths at a time when they are not expected to be used.

Finally, the user may wish to initially wear his or her robe on the trek out to the spa, and immediately prior to entering said spa, place the robe inside the device. Again, a battery powered, delayed start heater may warm the user's robe near to the time the user expects to leave the spa.

The mobility of the device allows it to be used in myriad locations, such as on a boat where one would take the device and after a day of waterskiing and swimming have dry clothes and towels in which to change. The fact that the clothes may be freshly warmed by the boat's power supply would be especially useful for aquatic search and rescue personnel, where a water victim may require warm clothing and towels to offset the effects of hypothermia.

The neutral center of gravity exhibited by the device in the upright position (that is, the position occupying the least surface space) allows the device or many numbers of the device to be easily balanced on a cart or floor space. One anticipated use is to move many numbers of the device to a location where multiple users await, and the neutral balanced nature of the device facilitates the dense packing of many units over a small area.

Although the garment warmer will warm any type of cloth, fabric or garments placed within it, certain methods of folding the garment create a more energy efficient environment for heating. For instance, the most efficient method of folding a robe for the garment warmer involves folding the robe lengthwise into thirds with the inside of the robe facing outwards and then folding the robe in half again. This will ensure that the inside of the robe (that which presses against the skin) is the warmest. Directions for the optimal folding of a robe may be provided with the device.

In order to make the device easier to use, the temperature and timer controls, if provided, can be easily adjusted. For instance, a set of timer buttons marked with an up and down arrow and a set of temperature buttons marked with an up and down arrow may be used. To ease opening and closing, latches that automatically snap to the locked position under the force of the closing lid may be used. To ease the opening process when performed by wet and slippery hands, soft edges and a textured ergonomic material may be used on the inside of the latch. Finally, said latches and handle may fold to a position flush with the outer edge of the device, thereby eliminating protruding surfaces that could potentially harm a user.

One skilled in the art will appreciate that the present invention can be practiced by other than the preferred embodiments, which are presented for purposes of illustration and not of limitation.

We claim:

1. A portable cloth warming device comprising:
   a. a liquid-resistant case defining an interior area substantially protected from liquid external to said case;
   b. a base member and a lid member connected for movement relative to one another by a hinge member;
   c. an insulating seal compressible between said base member and said lid member;
   d. at least two heating elements within said interior area, said heating elements electrically controllable by a thermostat;
   e. wherein said portable cloth warming device is substantially box shaped, having a first, second, third, fourth, fifth, and sixth side, and wherein each of said third, fourth, fifth and sixth sides has less than one half the surface area of either said first or said second side;
   f. wherein said case exhibits a substantially neutral center of gravity when standing on one of said third, fourth, fifth, or sixth sides;
   g. wherein said case comprises a set of foot pads on one of said first, second, third, fourth, fifth, or sixth side;
   h. a second set of footpads on a second of said sides of said case;
   i. a first storage area and a second storage area separated by one of said heating elements; and a third heating element.

2. The cloth warming device according to claim 1 wherein said third heating element is affixed to said lid member.

3. The cloth warming device according to claim 2 further comprising a battery.

\* \* \* \* \*